United States Patent [19]

King et al.

[11] Patent Number: 5,276,123

[45] Date of Patent: Jan. 4, 1994

[54] ALKOXY ENDBLOCKED POLYDIORGANOSILOXANE AND ROOM TEMPERATURE VULCANIZABLE SILICONE ELASTOMERS MADE THEREFROM

[75] Inventors: Russell K. King; Chi-long Lee, both of Midland, Mich.

[73] Assignee: Dow Corning Corporation, Midland, Mich.

[21] Appl. No.: 940,158

[22] Filed: Sep. 3, 1992

[51] Int. Cl.$^5$ .............................................. C08G 77/04
[52] U.S. Cl. .................................... 528/17; 528/33; 528/34; 528/37; 528/38; 524/863; 524/864; 556/425
[58] Field of Search ............... 556/425; 528/17, 34, 528/33, 37, 38; 524/863, 864

[56] References Cited

U.S. PATENT DOCUMENTS

| | | | |
|---|---|---|---|
| 3,122,522 | 2/1964 | Brown et al. | 260/46.5 |
| 3,146,250 | 8/1964 | Speier | 556/425 |
| 3,170,941 | 2/1965 | Speier | 556/425 |
| 3,175,993 | 3/1965 | Weyenberg | 260/46.5 |
| 3,334,067 | 8/1967 | Weyenberg | 260/46.5 |
| 3,383,355 | 5/1968 | Cooper | 260/46.5 |
| 3,661,816 | 5/1972 | Pepe et al. | 528/38 |
| 3,856,839 | 12/1974 | Smith et al. | 260/429.5 |
| 4,111,890 | 9/1978 | Getson et al. | 260/375 B |
| 4,438,039 | 3/1984 | Beers et al. | 260/429.5 |
| 4,579,964 | 4/1986 | Totten et al. | 556/434 |
| 4,683,278 | 7/1987 | Suzuki | 528/32 |
| 4,731,411 | 3/1988 | Lucas | 524/860 |
| 4,888,404 | 12/1989 | Klosowski et al. | 528/15 |
| 4,962,174 | 10/1990 | Bilgrien | 528/15 |
| 5,110,967 | 5/1992 | King et al. | 556/407 |
| 5,118,777 | 6/1992 | Okawa | 528/34 |

FOREIGN PATENT DOCUMENTS

2500020 7/1976 Fed. Rep. of Germany.
3902483 9/1989 Fed. Rep. of Germany.

*Primary Examiner*—Ralph H. Dean
*Attorney, Agent, or Firm*—Roger H. Borrousch

[57] ABSTRACT

An alkoxy endblocked polydiorgansiloxane of the formula

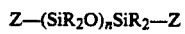

where Z is

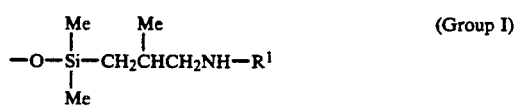 (Group I)

or

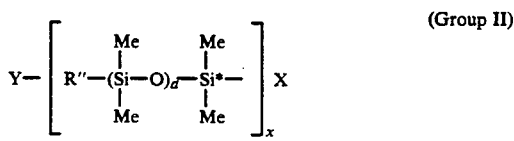 (Group II)

where Y is

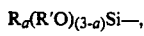

,

X is

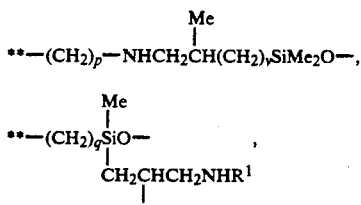

,

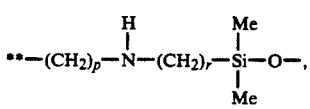

, (Abstract continued on next page.)

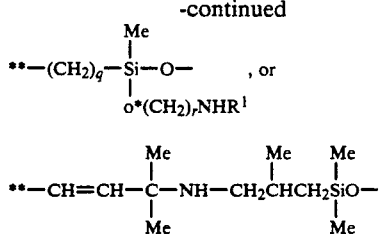

**—CH=CH—C(Me)(Me)—NH—CH₂CH(Me)CH₂SiO— in which a is 0 or 1, d has a value of 1 to 3 inclusive, v is 0 or 1, $n \leq 8$, p has a value of 3 to 6 inclusive, q has a value of 2 to 6 inclusive, r has a value of 4 to 6 inclusive, w is 0 or 1, Me is methyl, $R^1$ is an alkyl radical having from 1 to 6 inclusive carbon atoms, each R is a monovalent radical independently selected from the group consisting of hydrocarbon radicals and halogenated hydrocarbon radicals, R' is an alkyl radical of 1 to 3 inclusive carbon atoms, R" is a divalent hydrocarbon radical selected from the group consisting of —(CH₂)$_b$— and —CH(Me)(CH₂)$_c$—, b is from 2 to 6 inclusive, c is from 0 to 4 inclusive, the bond at ** is attached to the silicon atom Si*, can be used as the base polymer for making one package room temperature vulcanizable silicone elastomer compositions by combining it with alkoxysilane, titanium catalyst and filler. These RTV's cure rapidly and exhibit adhesion to substrates upon which they are cured.

55 Claims, No Drawings

ALKOXY ENDBLOCKED POLYDIORGANOSILOXANE AND ROOM TEMPERATURE VULCANIZABLE SILICONE ELASTOMERS MADE THEREFROM

BACKGROUND OF THE INVENTION

1. Field of the Invention

This invention relates to alkoxy functional polydiorganosiloxanes, a method of their preparation, and room temperature vulcanizable silicone elastomers made using the alkoxy functional polydiorganosiloxanes.

2. Background Information

One of the methods of producing silicone sealants is based upon the use of alkoxy endblocked polymers and a titanium catalyst. Such sealants are stable in the absence of moisture, but cure in the presence of moisture to a silicone elastomer. A distinguishing feature of this system over other moisture-curing systems is the absence of acidic or corrosive by-products produced during the curing process.

In storage tubes, many moisture curing sealants often exhibit, over long storage periods, gradual curing due to reaction with moisture. When use of this sealant is attempted, the sealant cannot be expelled from the storage tube because it is too viscous or it has completely cured. In contrast to this, the alkoxy-titanate room temperature vulcanizable (RTV) silicone elastomer compositions gradually loose the ability to cure with time of storage. This is particularly undesirable because the sealant can be expelled from the tube into the desired location for sealing without the user being aware that there is anything wrong. It is only after the sealant fails to cure that a problem becomes apparent, and by then it is too late as the sealant is already in place. It is then necessary to physically remove all of the old non-curing sealant and replace it with new. This is a very time consuming and expensive process. Because of this type of failure mode, it became imperative that a method of producing a non-acid, non-corrosive RTV silicone sealant be developed that would overcome this non-curing failure upon storage.

There are many patents directed to producing silicone sealants based upon the use of alkoxy functional polymers, alkoxy functional crosslinkers, and titanate catalysts. Representative of these is U.S. Pat. No. 3,334,067, issued Aug. 1, 1967, to Weyenberg. Weyenberg discloses a method of making one component room temperature curing siloxane rubber. His compositions are stable in the absence of moisture, but cure upon exposure to moisture. The method comprises mixing in the absence of moisture a hydroxy endblocked siloxane polymer, a silane of the formula $R^*Si(OR^{**})_3$ and a beta-dicarbonyl titanium compound. $R^*$ is a monovalent hydrocarbon radical, a monovalent halohydrocarbon radical, or a monovalent cyanoalkyl radical all having from 1 to 18 carbon atoms per radical. $R^{**}$ is an aliphatic hydrocarbon radical or a haloaliphatic hydrocarbon radical of less than 5 carbon atoms per radical.

In U.S. Pat. No. 3,383,355, issued May 14, 1968, Cooper discloses polymers having alkoxy groups bonded to terminal silicon atoms by reacting a hydroxylated organosiloxane polymer with an alkoxy silane in the presence of a suitable catalyst. He discloses that such functional diorganopolysiloxanes having from two to three alkoxy radicals attached to each terminal silicon atom are curable to a rubbery material in the presence of moisture and a suitable hydrolysis and condensation catalyst.

Smith et al., in U.S. Pat. No. 3,856,839, issued Dec. 24, 1974, disclose alkanedioxy titanium chelates which catalyze the cure of a composition which also contains methyltrimethoxysilane and a silanol chain-stopped polydiorganosiloxane fluid. The alkanedioxy titanium chelates are stated to be desirable because they do not cause thickening during the manufacture of the composition as do the previously known titanium compounds.

An improved version of the Smith et al compositions is disclosed by Getson et al. in U.S. Pat. No. 4,111,890, issued Sep. 5, 1978, in which the hydrocarbonoxy groups linked to the organopolysiloxane, organosilicon compound and the titanium ester groups are the same. They disclose that previous compositions have a short shelf-life even when kept under substantially anhydrous conditions, and that the longer these compositions are stored, the property profile deteriorates.

Beers et al in U.S. Pat. No. 4,438,039, issued Mar. 20, 1984, disclose that the shelf life of some commercial compositions was determined by an appearance problem, manifesting itself in the formation of various sizes of crystals ranging from fine sand-like to pellet-like particles. This patent discloses a particular titanium catalyst which does not form nodules upon storage.

The above prior art does not disclose solutions for the problem of failure to cure after prolonged storage. After an extensive investigation into the possible causes of such a storage failure, the solution to the problem was discovered. Once the solution to the problem is known, other background information becomes of interest.

Brown et al in U.S. Pat. No. 3,122,522, issued Feb. 25, 1964, disclose a siloxane composition, each molecule of which consists essentially of at least two units of the formula

and units of the formula

where each e has a value ranging from 2 to 3, each f has a value ranging from 0 to 1, the sum of e and f in any unit is no greater than 3, each g has a value ranging from 1 to 2, each h has a value ranging from 0 to 2, $R^*$ and $R^{**}$ are selected from monovalent hydrocarbon radicals and halogenated monovalent hydrocarbon radicals, M is a divalent hydrocarbon radical of from 2 to 18 inclusive carbon atoms, and M is free of aliphatic unsaturation. Each molecule of the silicone composition has an average of from 1.3 to 2 $R^*$ groups per silicon atom and there are at least 7 units of $R^*_hSiO_{(4-h)/2}$ per molecule.

U.S. Pat. No. 3,175,993, issued Mar. 30, 1965 to Weyenberg discloses a composition consisting essentially of the average formula

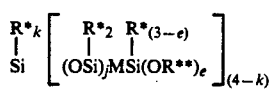

in which each $R^*$ is free of aliphatic unsaturation, M is a divalent hydrocarbon radical free of aliphatic unsaturation, k has a value of from 0 to 2 inclusive, j has a value of at least 3 and e has an average value from 2 to 3 inclusive.

Both Brown et al and Weyenberg teach preparation of the siloxane by reacting siloxanes containing —SiH groups with the appropriate silane containing an olefinic unsaturated aliphatic or cycloaliphatic group in the presence of a platinum catalyst through the reaction of the —SiH and aliphatic C=C group. This reaction produces the divalent M radical. Alternatively, the C=C group can be on the siloxane and the —SiH can be on the silane.

Lucas in U.S. Pat. No. 4,731,411, issued Mar. 15, 1988, discloses a process for producing alkoxy-terminated polysiloxanes useful to produce room temperature vulcanizing silicone rubber compositions. The process anhydrously reacts a silanol or vinyl siloxane with a poly-alkoxy crosslinking agent which is an alkoxy silane in the presence of a platinum catalyst. This alkoxy-terminated polysiloxane can also be mixed with treated filler and condensation catalyst. This application teaches that an alkoxy-terminated polysiloxane having no silethylene linkage at the polymer terminal silicon is equivalent to a polydiorganosiloxane that does contain a trialkoxysilethylene terminal group.

Totten et al in U.S. Pat. No. 4,579,964, issued Apr. 1, 1986, disclose an alkoxysilyl functional silicone including at least one functional group of the formula

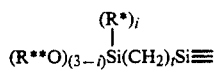

where t is an integer of from 2 to about 20, which is useful for imparting lubricity and softness to a variety of textile fabrics.

Klosowski et al in U.S. Pat. No. 4,888,404, issued Dec. 19, 1989, describe making silicone sealants which have improve shelf life. These silicone sealants are based on polymers of the general formula

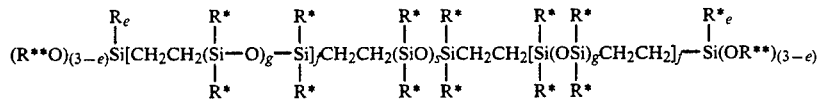

where R* is methyl, ethyl, propyl, phenyl, or trifluoropropyl, R** is methyl, ethyl, propy, or butyl, e is 0 or 1, f is 0 or 1, g is from 1 to 6 and s is such that the viscosity is from 0.5 to 3000 Pa.s at 25° C. These polymers are called alkoxysilethylene ended polydiorganosiloxanes. RTV silicone sealants are made by combining these polymers with alkoxysilane crosslinkers, titanium catalysts, and fillers. Klosowski et al improve the shelf stability of RTV silicone sealants through the use of their polymers, also improve the cure rate while maintaining or improving the storage stability of the RTV sealants.

SUMMARY OF THE INVENTION

This invention relates to a polydiorganosiloxane comprising an alkoxy endblocked polydiorganosiloxane of the following general formula

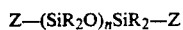

where Z is

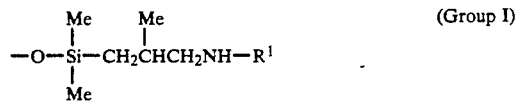

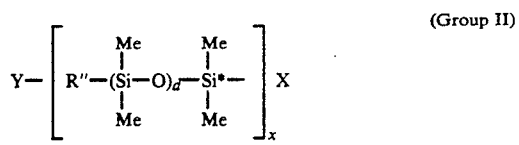

where Y is $R_a(R'O)_{(3-a)}Si—$,

X is

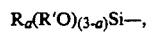

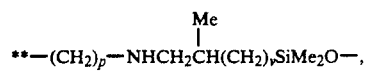

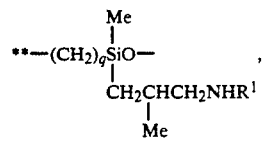

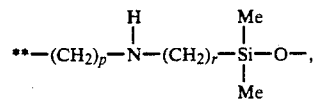

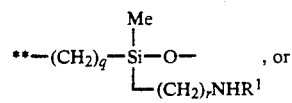

in which a is 0 or 1, d has a value of 1 to 3 inclusive, v is 0 or 1, n≧8, p has a value of 3 to 6 inclusive, q has a value of 2 to 6 inclusive, r has a value of 4 to 6 inclusive, w is 0 or 1, Me is methyl, R is a monovalent radical selected from the group consisting of hydrocarbon radicals and halogenated hydrocarbon radicals, R¹ is an alkyl radical having from 1 to 6 inclusive carbon atoms, R' is an alkyl radical of 1 to 3 inclusive carbon atoms, R" is a divalent hydrocarbon radical selected from the group consisting of —(CH₂)ᵦ— and —CH(Me)(CH₂)ᶜ—, b is from 2 to 6 inclusive, c is from 0 to 4 inclusive, and the bond at ** is attached to the silicon atom Si*.

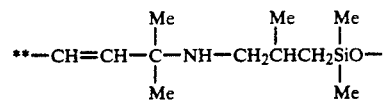

This invention also relates to a method of preparing the alkoxy endblocked polydialkylsiloxanes comprising mixing an azasilacycloalkyl functional alkoxysilane selected from the group consisting of

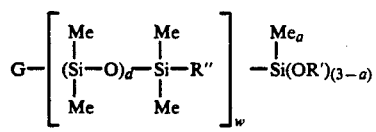
Formula (A)

in which G is an azasilacycloalkyl group selected from the group consisting of

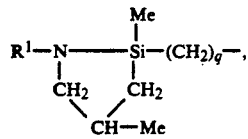
Formula (B)

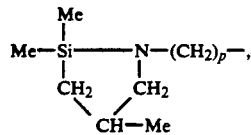
Formula (C)

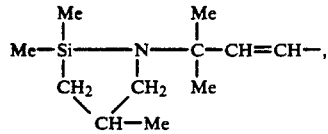
Formula (D)

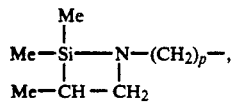
Formula (E)

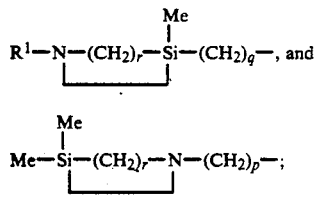
Formula (F)

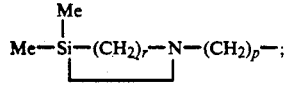
Formula (G)

in which $R^1$ is an alkyl radical of from 1 to 6 inclusive carbon atoms, R' is an alkyl radical of from 1 to 3 carbon atoms, R" is a divalent hydrocarbon radical selected from the group consisting of —(CH$_2$)$_b$— and —CH(Me)(CH$_2$)$_c$—, b is from 2 to 6 inclusive, c is from 0 to 4 inclusive, Me is methyl, a is 0 or 1, d has a value of 1 to 3 inclusive, w is 0 or 1, p has a value of 3 to 6 inclusive, q has a value of 2 to 6 inclusive, and r has a value of 4 to 6 inclusive with a silanol terminated polydiorganosiloxane of the general formula

where each R is a monovalent hydrocarbon radical independently selected from the group consisting of hydrocarbon radicals and halogenated hydrocarbon radicals and $n \geq 8$.

This invention also relates to a one package room temperature vulcanizable silicone elastomer comprising a product which is storage stable in the absence of moisture and curable to an elastomeric product when exposed to moisture and obtained by mixing (A) an alkoxy endblocked polydiorganosiloxane of the following general formula

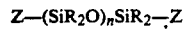

where Z is

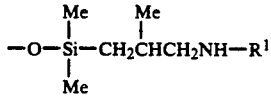
(Group I)

or

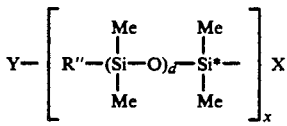
(Group II)

where Y is $R_a(R'O)_{(3-a)}Si—$,

X is

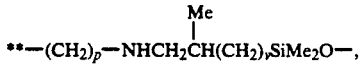

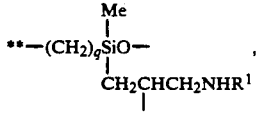

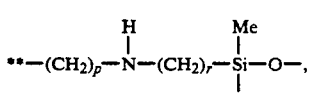

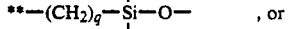

, or

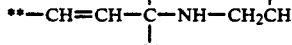

in which a is 0 or 1, d has a value of 1 to 3 inclusive, v is 0 or 1, $n \geq 8$, p has a value of 3 to 6 inclusive, q has a value of 2 to 6 inclusive, r has a value of 4 to 6 inclusive, w is 0 or 1, Me is methyl, $R^1$ is an alkyl radical of from 1 to 6 inclusive carbon atoms, each R is a monovalent radical independently selected from the group consisting of hydrocarbon radicals and halogenated hydrocarbon radicals, R' is an alkyl radical of 1 to 3 inclusive carbon atoms, R" is a divalent hydrocarbon radical selected from the group consisting of —(CH$_2$)$_b$— and —CH(Me)(CH$_2$)$_c$—, b is from 2 to 6 inclusive, c is from 0 to 4 inclusive, the bond at ** is attached to the silicon atom Si*, and in the alkoxy endblocked polydiorganosiloxane at least one Z is Group II, (B) an alkoxysilane, (C) a titanium catalyst, and (D) a filler.

DETAILED DESCRIPTION OF THE INVENTION

The azasilacycloalkyl functional alkoxysilanes used to make the alkoxy endblocked polydiorganosiloxane are selected from those compounds defined by Formula (A).

An azasilacycloalkyl functional alkoxysilane in which w is 0 can be made by reacting, in the presence of a platinum catalyst, an aliphatic unsaturated azasilacycloalkane with an alkoxysilane of the formula

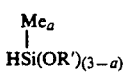

in which a is 0 or 1.

The azasilacycloalkyl functional alkoxysilanes where w is 1 can be made by reacting, in the presence of a platinum catalyst, an azasilacycloalkane containing aliphatic unsaturation with a dimethylsiloxane endblocked with hydrogen atoms of the formula

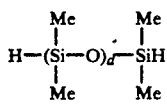

Formula (H)

where d has a value of 1 to 3 inclusive, and which in turn is reacted with an alkoxysilane having aliphatic unsaturation in the presence of a platinum catalyst. Methods of preparing various azasilacycloalkyl functional alkoxysilanes are illustrated in the following description.

An azasilacyclopentyl functional alkoxysilane of Formula (A) where G is Formula (C) and w is 1 can be prepared by reacting a hydrogen ended dimethylsiloxane of Formula (H), such as 1,1,3,3-tetramethyldisiloxane, with 1-(alken-1-yl)-2,2,4-trimethyl-1-aza-2-silacyclopentane in the presence of a platinum catalyst. 1-Aza-2-sila-cyclopentyl functional alkoxysilanes in which p is 3, 4, 5, or 6 can be prepared by using for the 1-(alken-1-yl)-2,2,4-trimethyl-1-aza-2-silacyclopentane, 1-allyl-2,2,4-trimethyl-1-aza-2-silacyclopentane, 1-(buten-1-yl)-2,2,4-trimethyl-1-aza-2-silacyclopentane, 1-(penten-1-yl)-2,2,4-trimethyl-1-aza-2-silacyclopentane, or 1-(hexen-1-yl)-2,2,4-trimethyl-1-aza-2-silacyclopentane. The resulting product is 1-(3-(2,2,4-trimethyl-1-aza-2-silacyclopentyl)propyl)-1,1,3,3-tetramethyldisiloxane when 1,1,3,3-tetramethyldisiloxane is used for the hydrogen dimethylsiloxane of Formula (H). This reaction is preferably carried out by heating under conditions which prevents the ingress of moisture or water into the reaction mixture. In a preferred method, the tetramethyldisiloxane, a small amount of the 1-aza-2-silacyclopentane, and platinum catalyst are heated and the remainder of the 1-aza-2-silacyclopentane is then slowly added. The amount of the 1-aza-2-silacyclopentane is such that the moles of the tetramethyldisiloxane exceed the moles of azasilacyclopentane. The product preferably is recovered by distillation. The following equation illustrates the reaction

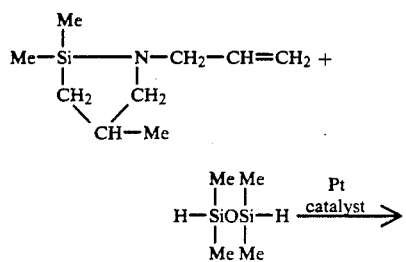

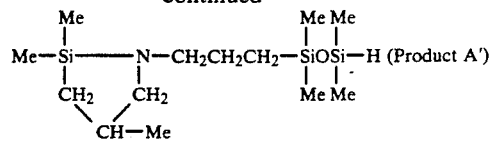

Product A' is 1-(3-(2,2,4-trimethyl-1-aza-2-silacyclopentyl)propyl)-1,1,3,3-tetramethyldisiloxane. Product A' is further reacted with either methylalkenyldialkoxysilane or alkenyltrialkoxysilane to make the azasilacyclopentyl functional alkoxysilane Formula (A). Examples of methylalkenyldialkoxysilane include methylvinyldimethoxysilane, methylvinyldiethoxysilane, methylvinyldipropoxysilane, methylvinyldiisopropoxysilane, methylallyldimethoxysilane, methylallyldiethoxysilane, methyl-allyldipropoxysilane, methylbuten-1-yldi-methoxysilane, methylpenten-1-yldimethoxysilane, methylpenten-1-yldiethoxy-silane, methylhexen-1-yldimethoxysilane, and methyl-hexen-1-yldiethoxysilane. Examples of alkenyltrialkoxysilane include vinyltrimethoxysilane, vinyltriethoxysilane, vinyltripropoxysilane, allyltrimethoxysilane, allyltriethoxysilane, allyltripropoxysilane, buten-1-yltrimethoxysilane, buten-1-yltriethoxysilane, buten-1-yltripropoxysilane, penten-1-yltrimethoxysilane, penten-1-yltriethoxysilane, penten-1-yltripropoxysilane, hexen-1-yltrimethoxysilane, and hexen-1-yltriethoxysilane. Product A' is combined with an alkoxysilane in the presence of platinum catalyst and preferably heated to cause the alkenyl group of the alkoxysilane to add across the Si-H group of Product A'. This reaction is illustrated by the following equation:

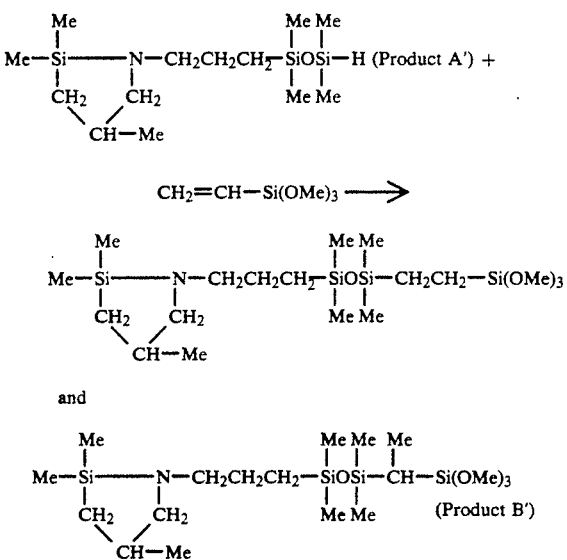

Product B' is a mixture of 1-(3-(2,2,4-trimethyl-1-aza-2-silacyclopentyl)propyl)-3-(2-trimethoxysilylethyl)-1,1,3,3-tetramethyldisiloxane and 1-(3-(2,2,4-trimethyl-1-aza-2-silacyclopentyl)propyl)-3-(1-trimethoxysilylethyl)-1,1,3,3-tetramethyldisiloxane. Product B' can be further purified by distillation of the reaction product under reduced pressure.

An azasilacyclopentyl functional alkoxysilane of Formula (A) where G is Formula (B) can be prepared by reacting an alkoxysiloxane having a hydrogen functional end of the formula

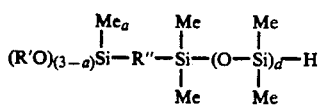 Formula (I)

in which a is 0 or 1, d has a value of 1 to 3 inclusive, and Me is methyl, with 1,2,4-trimethyl-2-alkenyl-1-aza-2-silacyclopentane in the presence of a platinum catalyst. The hydrogen ended alkoxysiloxanes of Formula (I) can be prepared by reacting an aliphatic unsaturated alkoxysilane with a hydrogen ended dimethylsiloxane of Formula (H) in the presence of a platinum catalyst. The preparation of 1-aza-2-silacyclopentyl functional alkoxysilanes of Formula (A) where G is Formula (B) can be illustrated by 1-(n*-trimethoxysilylalkyl)-1,1,3,3-tetramethyldisiloxane (Disiloxane A''); 1-(1-methyl-n*-trimethoxysilyl-alkyl)-1,1,3,3-tetramethyldisiloxane (Disiloxane B'') where n* depends upon the particular alkenyl group used; or a mixture of these reacted with 1,2,4-trimethyl-2-vinyl-1-aza-2-silacyclopentane in the presence of a platinum catalyst. This reaction is preferably carried out by heating under conditions which prevent the ingress of moisture or water into the reaction mixture. Disiloxanes A'' and B'' can be prepared by reacting $R'Me_aSi(OR)_{(3-a)}$ in which R' is an alken-1-yl radical having from 2 to 6 carbon atoms with $HMe_2Si\text{-}OSiMe_2H$ in the presence of a platinum catalyst. The alken-1-yl alkoxysilanes are illustrated above. The method for preparing Disiloxanes A'' and B'' are further described by Klosowski et al in U.S. Pat. No. 4,888,404, issued Dec. 19, 1989, which is hereby incorporated by reference to show the disiloxanes and their preparation. The product is preferably recovered by distillation. The following equation illustrates the reaction

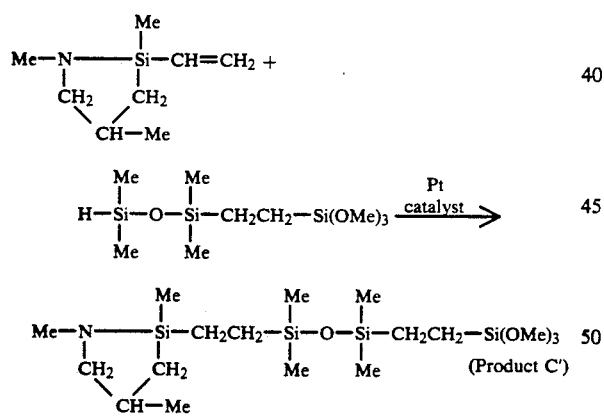

Product C' is 1-(2-(1,2,4-trimethyl-1-aza-2-silacyclopentyl)-ethyl)-3-(2-trimethoxysilylethyl)-1,1,3,3-tetramethyldisiloxane. The reaction product which contains Product C' can be further purified by distillation at reduced pressure. In the above reaction the Me (methyl radical) on the ring nitrogen atom is used for illustrative purposes as an example of $R^1$ which can be an alkyl radical selected from methyl, ethyl, propyl, butyl, pentyl, and hexyl. In the reactions which follow, in each case where a methyl is shown on the ring nitrogen atom, it is used as the preferred alkyl radical for $R^1$.

The aliphatic unsaturated azasilacyclopentanes used to make the azasilacyclopentyl functional alkoxysilanes of Formula

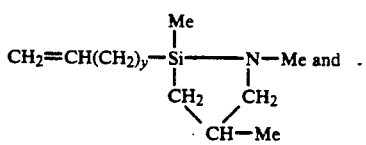 (I)

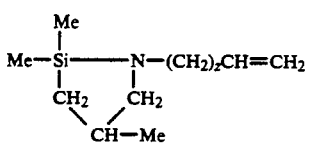

in which y has a value of from 0 to 4 inclusive; z has a value of from 1 to 4 inclusive; and Me is methyl radical. These azasilacyclopentanes are described in our U.S. Pat. No. 5,136,064, and incorporated by reference to show these azasilacyclopentanes and their preparation.

An azasilacyclopentyl functional alkoxysilanes of Formula (A) where G is Formula (D) can be made by the same method as the preparation for the azasilacyclopentyl functional alkoxysilanes of Formula (A) where G is Formula (C). In these preparations, the aliphatic unsaturated azasilacycloalkane has the formula

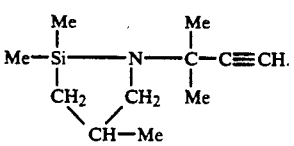

This azasilacycloalkane can be prepared by the method described in U.S. Pat. No. 5,136,064, where the reaction for the preparation is

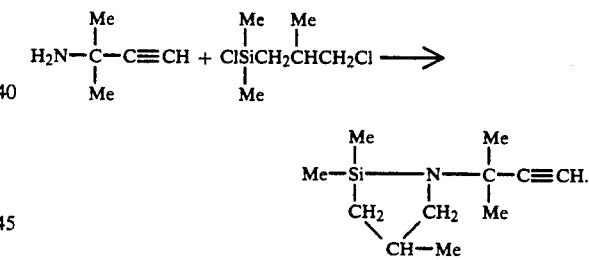

An azasilacyclobutyl functional alkoxysilane of Formula (A) where G is Formula (E) can be prepared by reacting a hydrogen ended dimethylsiloxane of Formula (H) with an azasilacyclobutane of the formula

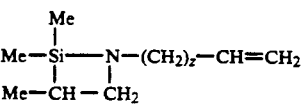

where z has a value of 1 to 4 inclusive. This reaction is done in the presence of a platinum catalyst and the following equation shows the reaction using 1,1,3,3-tetramethyldisiloxane as an example of the hydrogen ended dimethylsiloxane of Formula (H)

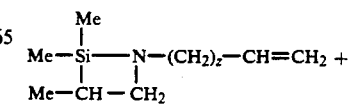

-continued

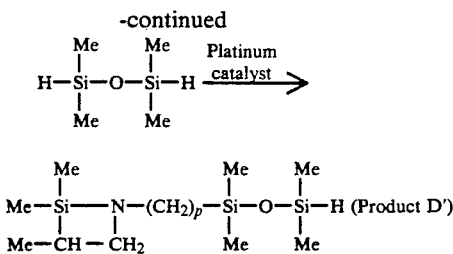

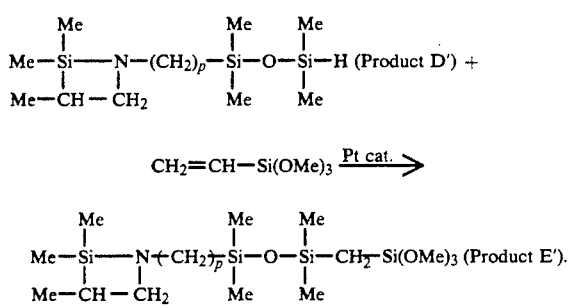

Product D' is further reacted with either methylalkenyldialkoxysilane or alkenyltrialkoxysilane to make the azasilacyclobutyl functional alkoxysilane Formula (A) where G is Formula (E). Examples of other alkoxysilanes which can be used are described above. Product D' is combined with an alkoxysilane in the presence of platinum catalyst and preferably heated to cause the alkenyl group of the alkoxysilane to add across the Si-H group of Product D'. This reaction is illustrated by the following equation:

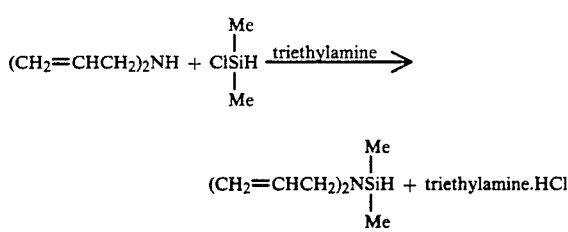

The preparation of an azasilacyclobutanes can be illustrated by the following: Diallylamine was reacted with chlorodimethylsilane in heptane in the presence of triethylamine to give diallylaminodimethylsilane as shown by the following equation $$(CH_2=CHCH_2)_2NH + ClSiH \xrightarrow{\text{Me}}_{\text{Me}} \xrightarrow{\text{triethylamine}}$$

$$(CH_2=CHCH_2)_2NSiH \underset{\text{Me}}{\overset{\text{Me}}{|}} + \text{triethylamine.HCl}$$

The silane product was obtained by ambient pressure distillation after removal of triethylamine hydrochloride by filtration. 1-allyl-2,2,3-trimethyl-1-aza-2-silacyclobutane was made by intramolecular hydrosilation of the diallyldimethylsilane. This reaction was carried out at 80° C. in the presence of PtCl$_2$(PPh$_3$)$_2$ in benzene. The starting material was consumed in four hours to give a product mixture of 83 mole percent of the azasilacyclobutane and 17 mole percent of azasilacyclopentane as illustrated by the following equation

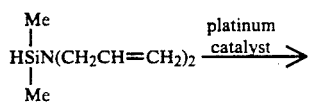

-continued

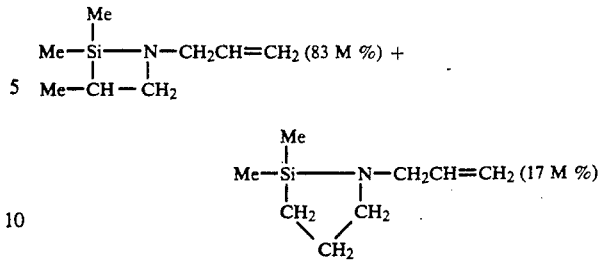

Total yield of product was 77 weight percent. The azasilacyclobutane can be reacted with 1,1,3,3-tetramethyldisiloxane in the presence of a platinum catalyst which in turn can be reacted with an alkoxysilane having aliphatic unsaturation as described above to make an azasilacyclobutyl functional alkoxysilane of Formula (A).

An azasilacycloalkyl functional alkoxysilane of Formula (A) where G is Formula (F) can be prepared by reacting a hydrogen ended dimethylsiloxane of Formula (H) with an azasilacycloalkane of the formula

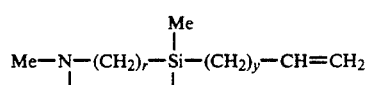

where y has a value of 0 to 4 inclusive and r has a value of 4 to 6 inclusive. This reaction is done in the presence of a platinum catalyst and the following equation shows the reaction using 1,1,3,3-tetramethyldisiloxane as an example of a hydrogen ended dimethylsiloxane of Formula (H)

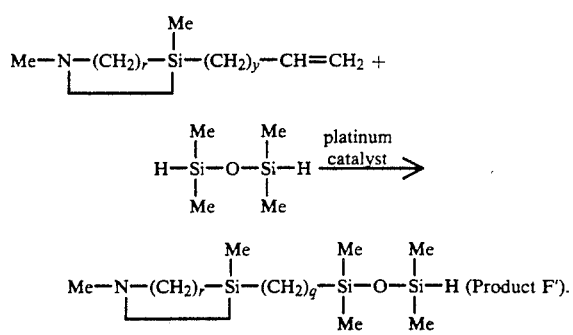

Product F' is further reacted with either methylalkenyldialkoxysilane or alkenyltrialkoxysilane to make the azasilacycloalkyl functional alkoxysilane Formula (A) where G is Formula (F). Examples of other alkoxysilanes which can be used are described above. Product F' is combined with an alkoxysilane in the presence of platinum catalyst and preferably heated to cause the alkenyl group of the alkoxysilane to add across the Si-H group of Product F'. This reaction is illustrated by the following equation:

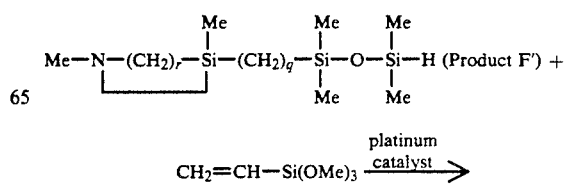

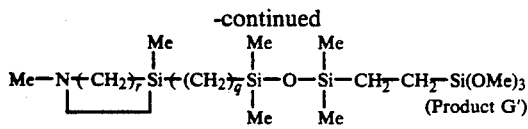

An azasilacycloalkane used to provide the functionality of Formula (F), 2-vinyl-1,2-dimethyl-1-aza-2-silacycloalkane, can be made by reacting

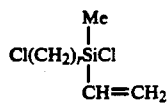

where r has a value of 4 to 6 inclusive, with methylamine using the procedure described in U.S. Pat. No. 3,146,250, issued Aug. 25, 1964, to Speier which is hereby incorporated by reference to show a method of preparation for azasilacycloalkanes. The chlorosilane of the formula

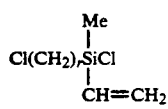

can be made by reacting

with vinyl magesium bromide, followed by reaction with acetyl chloride in the presence of ferric trichloride catalyst. The methoxysilane of the formula

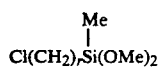

can be made by reacting

with $CH_2=CH-(CH_2)_{(r-2)}Cl$ in the presence of a platinum catalyst. Other reactions are describe in an article by Speier et al, in the Journal of Organic Chemistry, vol. 36, pages 3120–3126, (1971), entitled "Syntheses of (3-Aminoalkyl)silicon Compounds."

An azasilacycloalkyl functional alkoxysilane of Formula (A) where G is Formula (G) can be prepared by reacting a hydrogen ended dimethylsiloxane of Formula (H) with an azasilacycloalkane of the formula

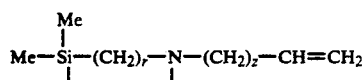

where z has a value of 1 to 4 inclusive. This reaction is done in the presence of a platinum catalyst and the following equation shows the reaction using 1,1,3,3-tetramethyldisiloxane as an example of a hydrogen ended dimethylsiloxane of Formula (H)

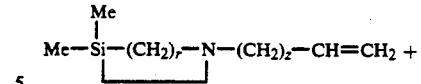

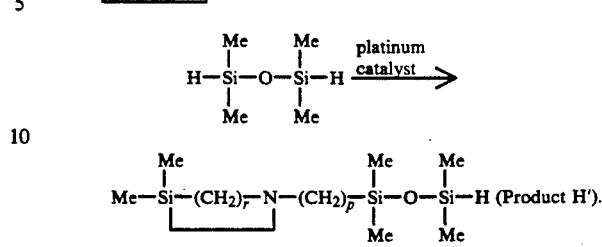

Product H' is further reacted with either methylalkenyldialkoxysilane or alkenyltrialkoxysilane to make the azasilacycloalkyl functional alkoxysilane Formula (A) where G is Formula (G). Examples of other alkoxysilanes which can be used are described above. Product H' is combined with an alkoxysilane in the presence of platinum catalyst and preferably heated to cause the alkenyl group of the alkoxysilane to add across the Si-H group of Product H'. This reaction is illustrated by the following equation:

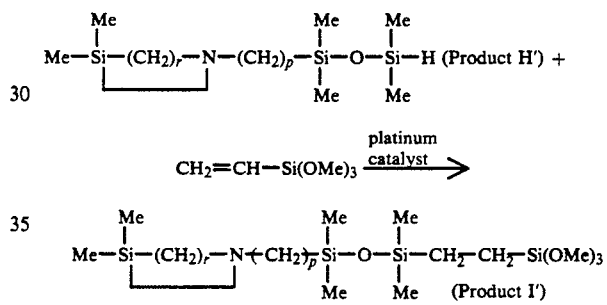

The 1-allyl-2,2-dimethyl-1-aza-2-silacycloalkanes can be made by reacting

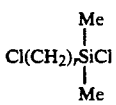

with $CH_2=CHCH_2NH_2$ using a procedure described in U.S. Pat. No. 3,146,250. The chlorosilane of the formula

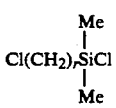

can be made by reacting

with $CH_2=CH(CH_2)_{(r-2)}Cl$ in the presence of a platinum catalyst.

The olefinic unsaturation of the 1-aza-2-silacyclopentane reacts with the Si-H group of the tetramethyldisiloxane in the presence of a platinum catalyst. This reaction is termed an "addition reaction" or a "hydrosilylation reaction" where the olefinic bond reacts with the silicon-bonded hydrogen such that the Si-H adds across the double bond. Platinum catalysts are well know in the art for catalyzing this reaction. These platinum catalysts include the chloroplatinic acid described by Speier et al in U.S. Pat. No. 2,823,218, issued Feb. 11, 1958; complexes of chloroplatinic acid with low molecular weight vinyl-containing polydiorganosiloxanes such as syn-divinyltetramethyldisiloxane as described by Willing in U.S. Pat. No. 3,419,593, issued Dec. 31, 1968; alkene complexes described by Ashby in U.S. Pat. No. 3,159,601, issued Dec. 1, 1964, and U.S. Pat. No. 3,159,662, issued Dec. 1, 1964; the platinum acetylacetonate described by Baney in U.S. Pat. No. 3,723,497, issued Mar. 27, 1973; the platinum alcoholates described by Lamoreaux in U.S. Pat. No. 3,220,972, issued Nov. 30, 1965; and in many more patents which describe various types of platinum catalysts. These patents describing platinum catalysts are hereby incorporated by reference to show the platinum catalysts and to show the hydrosilylation reaction.

The alkoxy endblocked polydiorganosiloxanes of this invention are prepared by mixing the azasilacycloalkyl functional alkoxysilanes as defined above with a silanol terminated polydiorganosiloxane of the general formula

HO—SiR₂O)ₙSiR₂OH where each R is a monovalent radical independently selected from the group consisting of hydrocarbon radicals and halogenated hydrocarbon radicals and $n \geq 8$. This reaction is rapid and goes to completion at room temperature without requiring a catalyst. This reaction should take place under conditions which prevent the ingress of moisture or water into the reaction mixture. The silanol terminated polydiorganosiloxanes are well known in the art and include those in which R is a monovalent hydrocarbon radical such as an alkyl radical, preferably from 1 to 6 carbon atoms, such as methyl, ethyl, propyl, isopropyl, butyl, isobutyl, tertiary butyl, pentyl, and hexyl; an aryl radical such as phenyl, tolyl, and xylyl; and a monovalent halogenated hydrocarbon radical such as 3,3,3-trifluoropropyl and gamma-chloropropyl. The silanol terminated polydiorganosiloxanes are preferably silanol terminated polydialkylsiloxanes praticularly those in which R is methyl and n has an average value of from 50 to 1,000. One advantage of this method is that it can be done continuously. The reaction between the silicon-bonded hydroxyl and the azasilacyclopentane group is fast enough that the alkoxy endblocked polydiorganosiloxanes of the present invention can be made continuously.

Alkoxy endblocked polydiorganosiloxanes of this invention can also be prepared in which one end of polymer is Group I and one end is Group II. Such alkoxy endblocked polydiorganosiloxanes are prepared as described above by including with the azasilacyclopentyl functional alkoxysilanes of Formula (A), 1,2,2,4-tetramethyl-1-aza-2-silacyclopentane. The azasilacycloalkyl functional alkoxysilanes produce Group II ends and the 1,2,2,4-tetramethyl-1-aza-2-silacyclopentane produces Group I ends. Group I ends do not become crosslinkages during ordinary exposure to moisture at room temperature and in an RTV composition. When both the 1,2,2,4-tetramethyl-1-aza-2-silacyclopentane and aza-silacyclopentyl functional alkoxysilanes are present in the reaction with hydroxyl endblocked polydiorganosiloxane, the results is a statistical mixture of three kinds of polymers. One type of polydiorganosiloxane is alkoxy endblocked polydiorganosiloxanes with Group II on both ends (Type 1). Another type of polydiorganosiloxane is alkoxy endblocked polydiorganosiloxane with Group I on one end and Group II on the other end (Type 2). The third type of polydiorganosiloxane is a polydiorganosiloxane in which both ends are Group I (Type 3). This third type does not contain silicon-bonded alkoxy groups and therefore would not enter into crosslinking reaction when exposed to moisture. The reaction product when hydroxyl endblocked polydiorganosiloxane, 1,2,2,4-tetramethyl-1-aza-2-silacyclopentane, and azasilacyclopentyl functional alkoxysilanes are combined, is a mixture of the three types of polydiorganosiloxanes. The greater the amount of 1,2,2,4-tetra-methyl-1-aza-2-silacyclopentane present in the reaction mixture, the higher the concentration of Type 3 polydiorganosiloxane. For this reason (because Type 3 are unreactive), the amount of 1,2,2,4-tetramethyl-1-aza-2-silacyclopentane used is that amount which is insufficient to produce polydiorganosiloxane with greater than 50% of the ends as Group I when the alkoxy endblocked polydiorganosiloxanes of this invention are to be used in the preparation of RTV compositions. The reaction products in which less than 30% of the ends are Group I are preferred for lowering the modulus of cured products from exposing RTV compositions to moisture. The higher the content of Group I ends in the polydiorganosiloxane mixture, the lower the crosslink density of cured RTV compositions prepared therefrom and the lower the modulus (other ingredients being equal).

The room temperature vulcanizable silicone elastomeric sealants prepared by using the alkoxy endblocked polydiorganosiloxanes of this invention cure rapidly and have excellent shelf life. The sealant is made from a mixture of (A) alkoxy endblocked polydiorganosiloxanes having the following general formula

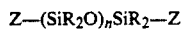
Z—(SiR₂O)ₙSiR₂—Z where Z is

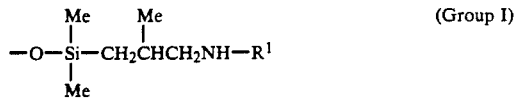
(Group I)

or

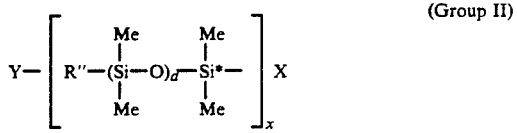
(Group II)

where Y is

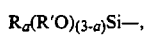
Rₐ(R'O)₍₃₋ₐ₎Si—,

X is

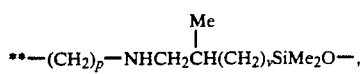
**—(CH₂)ₚ—NHCH₂CH(CH₂)ᵣSiMe₂O—,

-continued

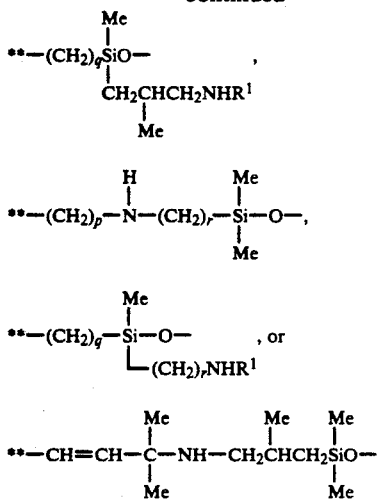

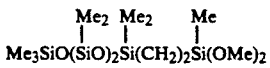

in which a is 0 or 1, d has a value of 1 to 3 inclusive, v is 0 or 1, n≥8, p has a value of 3 to 6 inclusive, q has a value of 2 to 6 inclusive, r has a value of 4 to 6 inclusive, w is 0 or 1, Me is methyl, $R^1$ is an alkyl radical having from 1 to 6 inclusive carbon atoms, each R is a monovalent radical independently selected from the group consisting of hydrocarbon radicals and halogenated hydrocarbon radicals, R' is an alkyl radical of 1 to 3 inclusive carbon atoms, R" is a divalent hydrocarbon radical selected from the group consisting of —$(CH_2)_b$— and —$CH(Me)(CH_2)_c$—, b is from 2 to 6 inclusive, c is from 0 to 4 inclusive, the bond at ** is attached to the silicon atom Si*, and in the alkoxy endblocked polydiorganosiloxane at least one Z is Group II, (B) an alkoxysilane, (C) a titanium catalyst, and (D) a filler.

These silicone sealants do not lose their ability to cure upon exposure to moisture after the sealant is stored for a long period of time in the absence of moisture. As was noted in the background information, it has been found that silicone elastomer sealants of the type based upon alkoxy endblocked polydiorganosiloxanes and titanate catalyst lose the ability to cure upon shelf aging. A study was undertaken to determine the cause of the loss of curability in the hope that a solution to the problem could then be determined. A model compound having —Si(Me)(OMe)$_2$ ends was reacted with tetrabutyltitanate (TBT) at 70° C. and the reaction products were analyzed. Me represents methyl and Vi represents vinyl. It was found that there was relatively large amounts of Me$_2$Si(OR)$_2$ where R was either methyl or butyl radical. Further studies showed that this difunctional product could only be produced by degradation of the dialkoxy functional polymer ends with the production of monoalkoxy ended polymer, destroying the model compound. It was known that a monoalkoxy ended polymer would not produce a cure in this type of cure system. Further testing showed that the reaction that was taking place was a reaction of the titanate catalyst with the end siloxy group of the polymer, removing it from the polymer and leaving an alkoxy group in its place. A method of preventing this reaction between the titanate and the end siloxy group of the polymer was then sought. A second model compound was prepared with the formula

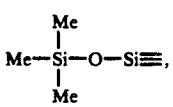

and this compound was combined with tetrabutyltitanate and heated at 70° C. for 70 days. At the end of that time there was no Me$_2$Si(OR)$_2$, showing that this could be a solution to the problem, since this model compound remained intact and no degradation had occurred as in the first case. These tests demonstrated that when the terminal silicon atom in the polymer has three carbon atoms attached as on the one end of this model compound, $$\text{Me}-\underset{\underset{\text{Me}}{|}}{\overset{\overset{\text{Me}}{|}}{\text{Si}}}-\text{O}-\text{Si}\equiv,$$

or when the oxygen atom between the penultimate silicon atom and the terminal silicon atom is replaced by a carbon linkage, as at the other end of this model compound, there is no reaction with the titanium catalyst, other than alkoxy exchange.

This discovery was then evaluated in a curable composition in the following manner. A dimethylhydrogensiloxy endblocked polydimethylsiloxane was mixed with an excess of vinyltrimethoxysilane in the presence of H$_2$PtCl$_6$ and heated overnight at 100° C. in the absence of moisture. The product was a polymer of the formula

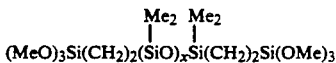

This polymer was combined with tetrabutyltitanate and heated at 70° C. for 8 weeks. At various times during this heating period, a sample of the polymer was deposited in an aluminum dish and exposed to the moisture in the air to evaluate the cure. All samples produced a tight, dry cure in 24 hours at room temperature. This showed that this might be a solution to the shelf stability problem. Further work established that silicone sealants could be produced using the method of this invention which had improved shelf life when compared to similar compositions not made with the alkylsilethylene ended polymer.

Alkoxysilane crosslinkers (B) are well known in the art. For example, those alkoxysilanes of the formula R$_x$Si(OR')$_{(4-x)}$ where R is methyl or phenyl, R' is methyl, ethyl, or propyl, and x is 0 or 1 is added as a moisture scavenger and as a modulus control agent. Preferred are the silanes in which there are three alkoxy groups present, such as methyltrimethoxysilane. The amount of crosslinker preferably is from 0.35 to 9.0 parts by weight per 100 parts by weight of alkoxy endblocked polydiorganosiloxane, with from 2 to 8 parts most preferred. It is possible to produce useful sealants without using a crosslinker when the polydiorganosiloxane (A) is present because of the functionality of the polymer itself, but from a practical viewpoint, the crosslinker is preferred because it contributes to the excellent shelf life of the sealant. It is also useful in controlling the degree of crosslinking in the cured elastomeric sealant; higher concentrations of the crosslinker results in a harder, lower elongation elastomer.

The sealant compositions of this invention are cured through the use of a titanium catalyst (C). The titanium catalyst can be any of those known to be useful for catalyzing the moisture induced reaction of alkoxy containing siloxanes or silanes. Preferred are a titanium catalyst such as titanium esters such as tetrabutyltitanate, tetraisopropyltitanate, tetra-2-ethylhexyl-titanate, tetraphenyltitanate, triethanolaminetitanate, organosiloxytitanium compounds such as those described in U.S. Pat. No. 3,294,739, and beta-dicarbonyl titanium compounds such as those described in U.S. Pat. No. 3,334,067, both patents being herein incorporated by reference to show titanium catalyst and methods of manufacture. Preferred catalysts include tetrabutyltitanate, tetraisopropyltitanate, and bis-(acetoacetonyl)-diisopropoxy titanium (IV). The amount of catalyst is from 0.2 to 6.0 parts by weight per 100 parts by weight of alkoxy endblocked polydiorganosiloxane (A). Preferred concentrations are from 0.5 to 3.0 parts by weight.

The RTV silicone sealant compositions of this invention contain a filler as one of the ingredients. These fillers are well known in the industry. They are added to the mixture to provide reinforcement of the polymer, to provide control of the flow characteristics of the sealant before curing, to control the physical properties of the sealant after curing, and to extend the bulk of the sealant to reduce the cost of the ingredients, as well as, to provide other desired characteristics such as opacity. Reinforcing fillers such as fume silica, precipitated silica, and diatomaceous earth are used to give the highest physical strengths to the sealants. Reinforcing fillers are generally recognized as being very fine particles having a surface area from about 50 to 700 $m^2/g$. These fillers may be untreated fillers or treated fillers where the treatment is used to modify the filler surface. Extending fillers such as titanium dioxide, zirconium silicate, calcium carbonate, iron oxide, ground quartz, and carbon black are commonly used. The amounts of filler used can obviously be varied within wide limits in accordance with the intended use. For example, in some cases the sealant could be used with no filler, but it would have very low physical properties. Reinforcing fillers are commonly used in amounts from about 5 to 50 parts by weight to give the highest physical properties, such as tensile strength. Extending fillers are finely ground in that the average particle size is in the range of from about 1 to 10 micrometers. Extending fillers are used in amounts as high as 500 parts by weight per 100 parts by weight of the alkoxy endblocked polydiorganosiloxane of (A).

Other ingredients which are commonly used in RTV silicone sealant compositions can also be used in this invention such as colorants, flame retardant additives, plasticizers, compression set additives, and modulus control additives.

The RTV silicone sealant compositions are preferably made by mixing the alkoxy endblocked polydiorganosiloxane of (A) with filler (D) until a uniform mixture is obtained. The mixing process can be carried out with a low shear mixer or stirrer in the case of the extending fillers or with a high shear mixer such as a dough mixer or 3-roll mill in the case of the reinforcing fillers. After (A) and (D) are mixed, it is desirable to place them in a container and centrifuge them to remove any entrapped air (deairing). A deaired mixture of alkoxysilane crosslinker (B), and titanium catalyst (C) are added in the absence of moisture to the mixture of (A) and (D). They are thoroughly stirred to give a uniform mixture. The uniform mixture is then preferably deaired, aged 24 hours and again deaired by exposing the mixture to a vacuum to remove any volatiles from the mixture. The mixture is then sealed into storage containers, sealant tubes for example, to store it until it is to be used.

When the RTV silicone sealant composition is exposed to moisture, it cures to give an elastomeric product. The composition is useful as a sealant for filling spaces and gaps as may be found in buildings. These RTV silicone sealants exhibit improved adhesion to the substrates on which it is cured.

The following syntheses and examples are included for illustrative purposes only and should not be construed as limiting the invention, which is set forth in the appended claims. All parts are parts by weight, viscosities were measured at 25° C. unless otherwise indicated, Me=methyl, and Vi=vinyl.

SYNTHESIS 1

Preparation of 2,2,4-trimethyl-1-allyl-1-aza-2-silacyclopentane

The 2,2,4-trimethyl-1-allyl-1-aza-2-silacyclopentane was prepared as follows. Chlorodimethyl(3-chloro-2-methylpropyl)silane (100 g, 0.54 mol) was slowly added to 211.73 g (3.71 mol, 6.87 eq) of undistilled allyl amine resulting in an exothermic reaction. This reaction mixture was stirred at room temperature for 15 hours, heated to reflux at atmospheric pressure for 72 hours, and heated to 120° C. under about 50 psig pressure for 16 hours. The following GC-MS ratios shown in Table I exemplified the reactions progression and the spectra observed were as shown.

TABLE I

| RETENTION TIME, MIN | 15 HOURS 20° C. | 24 HOURS REFLUX | 72 HOURS REFLUX | 16 HOURS 120° C. | COMPOUND |
|---|---|---|---|---|---|
| 2.70 | 0.0 | 3.9 | 21.3 | 71.9 | E |
| 2.82 | 0.0 | 1.0 | 1.1 | 0.9 | F |
| 3.20 | 50.4 | 11.0 | 4.1 | 0.0 | G |
| 5.19 | 29.5 | 63.0 | 40.2 | 0.0 | H |
| 8.46 | 20.0 | 8.8 | 8.1 | 2.4 | I |
| 9.58 | 0.0 | 9.3 | 10.1 | 6.1 | J |
| 10.58 | 0.0 | 3.1 | 15.1 | 18.7 | K |

Compound E was 2,2,4-trimethyl-1-allyl-1-aza-2-silacyclopentane and the spectra was 169 (819), $M^+$; 154 (1326), $M^+-CH_3$; 142 (1074), $M^+-Vi$; 127 (375), $M^+-C_3H_6$; 126 (354), $M^+-C_3H_7$; 100 (784), M-69; 86 (8734), $Me_2SiN=CH_2^+$; 59 (10000), $Me_2SiH^+$. Compound F was not determined.

Compound G was chlorodimethyl(3-chloro-2-methylpropylsilane and the spectra was 184 (0), $M^+$; 169 (233), $M^+-Me$; 137 (292), $M^+-47$; 113 and 115 (2459 and 1991), $Cl_2MeSi^+$; 93 (9786), $ClMe_2Si^+$; 56 (10000), $C_4H_8$.

Compound H was allylaminodimethyl(3-chloro-2-methylpropyl)silane and the spectra was 205 (10), M+; 190 (79), M+—Me; 170 (153), M+—Cl; 149 (618), M+—C₄H₈; 134 and 136 (1263 and 508), M+—CH₃—C₄H₈; 120 and 122 (1250 and 625), unassigned; 114 (10000), CH₂=CHCH₂NHSiMe₂+; 98 (4709), unassigned; 93 and 95 (4999 and 1948), ClMe₂Si+.

Compound I was 1,1,3,3-tetramethyl-1,3-bis(3-chloro-2-methylpropyl)disiloxane and the spectra was 314 (0), M+; 187 and 189 (2045 and 1291), ClMe₂SiOSiMeCl+; 167 and 169 (10000 and 3897), ClMe₂SiOSiMe₂+.

Compound J was 1,1,3,3-tetramethyl-1-(3-chloro-2-methylpropyl)-1-(3-allylamino-2-methylpropyl)disiloxane and the spectra was 335 (0), M+; 320 (52), M+—Me; 167 and 169 (1216 and 463), ClMe₂SiOSiMe₂+; 70 (10000), CH₂=CHCH₂NH=CH₂+.

Compound K was 1,1,3,3-tetramethyl-1,3-bis(3-allylamino-2-methylpropyl)disiloxane and the spectra was 356 (0), M+; 170 (1017), CH₂=CHCH₂NHCH₂CH(CH₃)CH₂SiMe₂+; 169 (1177), peak 170-H; 70 (10000), CH₂=CHCH₂NH=CH₂+.

Upon cooling the product of the reaction, a two phase system resulted. The upper phase weighed 111.85 g and contained most of the product 2,2,4-trimethyl-1-allyl-1-aza-2-silacyclopentane. The lower phase weighed 177.12 g and was an amber viscous liquid. This lower phase was concentrated at atmospheric pressure with a pot temperature of 120° C. to 122 g. Another 4.0 g of the upper phase was separated upon cooling. The combined product phases were distilled under vacuum. After a slow evolution of allylamine, the product codistilled with an ammonium salt at 78° C. and 30 mmHg. Filtration gave 51.63 g (56% yield) of essentially pure 2,2,4-trimethyl-1-allyl-1-aza-2-silacyclopentane. The ¹³C NMR was: 138.13, vinyl; 114.39, vinyl; 58.98, allyl CH₂; 50.31, ring CH₂N; 31.88, CH; 21.94 and 21.50, SiCH₂ and C—Me; 0.22 and −0.76, SiMe. The ²⁹Si NMR spectra had one peak at 15.56 ppm relative to tetramethylsilane.

SYNTHESIS 2

Preparation of 1,2,4-Trimethyl-2-vinyl-1-aza-2-silacyclopentane

The 1,2,4-trimethyl-2-vinyl-1-aza-2-silacyclopentane was prepared as follows. To a solution of 50.0 g (254 mmol) of dimethoxy-methyl(3-chloro-2-methylpropyl)silane in 250 ml of diethyl ether in a three-necked, 1 L (liter) round-bottom flask fitted with a mechanical stirrer, nitrogen inlet, and addition funnel was added over a one hour, a solution of 290 ml(290 mmol) of 1M (molar) vinyl magnesium bromide in tetrahydrofuran (THF). The reaction was allowed to stir overnight under a nitrogen atmosphere at room temperature and the slightly yellowish liquid was decanted from the solids. The solvents were removed at 40° C. and 9 mmHg to yield 68.09 g of a yellow liquid with considerable amounts of solids. To this was added 50 ml of benzene and the salts were removed by filtration through a course glass frit funnel. The collected solids were washed with two 30 ml portions of benzene. The combined organic fractions were stripped at 50° C. and 9 mmHg to yield 40.19 g of liquid with a small amount of salts. The results of gas chromatography-mass spectroscopy (GC-MS) showed the following composition of the liquid:

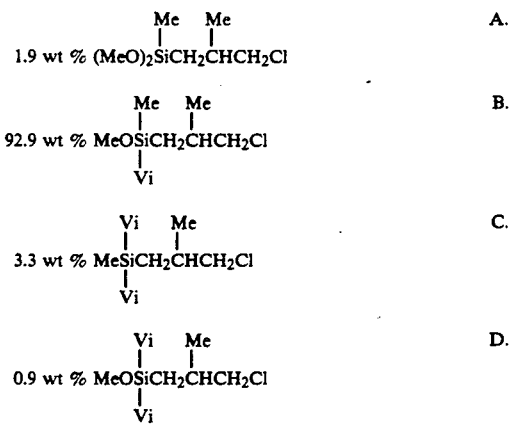

3.1 wt % of 9 unidentified impurities at an order of magnitude lower level.

The mass spectra was used to identify these compounds and the results were:

For B compound: 192, not observed, M+; 165(10), M—Vi; 137 (10),NA; 121(210), (MeO)ViClSi+; 109(230), (MeO)MeClSi+; 101(780), (MeO)MeViSi+; 56(1000), C₄H₈+ where data are presented as charge (m/e), (relative intensity).

For C compound: 188, not observed, M+; 161(8), M—Vi; 117 (280), Vi₂ClSi+; 105(284), MeViSi+; 97(489), Vi₂MeSi+; 56(1000), C₄H₈+.

For D compound: 204, not observed, M+; 177(10), M—Vi; 121 (290), (MeO)ViClSi+; 113(620), (MeO)-Vi₂Si+; 56(1000), C₄H₈+.

The ²⁹Si nuclear magnetic resonance(NMR) had one major peak at 6.63 ppm relative to tetramethylsilane. The crude product was purified by short path distillation. The fraction boiling at 75° C. at 6 mmHg weighed 28.22 g (58% yield) and was identified as compound B, methoxymethylvinyl(3-chloro-2-methylpropyl)silane.

Chloromethylvinyl(3-chloro-2-methylpropyl)silane was prepared as follows. A mixture of 28.00 g (143.3 mmol) of compound B in 15.5 ml (17.10 g, 217.9 mmol, 1.5 eq) of acetyl chloride was allowed to sit at ambient temperature for 12 hours. A slight exotherm was noted. The low boiling material was removed by distillation and the product distilled at 88° C. to 90.5° C. and 30 mmHg to give 25.2 g of material (88% yield). The product was chloromethylvinyl(3-chloro-2-methylpropyl)silane as was identified by ¹³C NMR: 134.79 and 134.73 and 134.68 (1:2:1, 1.67), SiVi; 52.93 (1.00), CH₂Cl; 31.51 and 31.48 (0.83), CH; 22.88 and 22.84 (0.97), CHMe; 20.13 and 20.10 (1.01), SiCH₂; 0.59 and 0.54 (0.68), SiMe and by ²⁹Si NMR: 17.81 and 17.78 (1:1) where data are presented as ppm (relative intensity).

Methylamine was condensed into a 1 L round-bottom flask and distilled from sodium. To 490 ml (340 g, 11 mol) of methylamine was slowly added 309.8 g (1.57 mol) of chloromethylvinyl(3-chloro-2-methylpropyl)silane, which resulted in two phases. The two phase system was transferred to a Parr reactor and heated at 110° C. and 230 psig for 10 hours. The reaction mixture was cooled to −10° C., transferred to a 2 L round-bottom flask and 400 ml of cold pentane was added. The layers were separated, and the upper organic phase concentrated. After concentration, some ammonium slats had precipitated. These salts were removed by filtration and the product purified by distillation at reduced pressure to yield about 160 g (60% yield) of 1-aza-2-silacyclopentane with a small amount of ammonium salts. The distilled product was 97% pure 1,2,4-trimethyl-2-vinyl-1-aza-2-silacyclopentane with two major higher boiling impurities (about 1wt % each) and numerous minor higher boiling impurities. The GC-MS data was: 1,2,4-Trimethyl-2-vinyl-1-aza-2-silacyclopentane, Retention Time 2.00 min; 155 (365), M+; 154 (243), M+—H; 140(97), M+—Me; 126 (113), M+—Vi; 113 (962, M+—$C_3H_7$; 112 (1000), M+—$C_3H_7$; 89 (396), MeViSiN=$CH_2$+; 71 (465) MeViSiH+. The $^{13}C$ NMR spectra was: 138.23 and 137.98, terminal vinyl; 132.86 and 137.98, internal vinyl; 62.19 and 61.92, N—$CH_2$; 33.93 and 33.80, methine; 32.09 and 32.06, NMe; 21.48 and 21.54, CHMe; 21.23 and 20.95 Si—$CH_2$; −3.43 and −4.29, SiMe. The $^{29}Si$ NMR had peaks at 6.229 and 6.039 relative to tetramethylsilane.

SYNTHESIS 3

Synthesis of 1-(3-(2,2,4-trimethyl-1-aza-2-silacyclopentyl)-propyl)-3-(2-trimethoxysilylethyl)-1,1,3,3-tetramethyldisiloxane To 169 g (1.26 mol) of 1,1,3,3-tetramethyldisiloxane, 0.25 g of a chloroplatinic acid-1,3-divinyl-1,1,3,3-tetramethyldisiloxane complex having about 0.7 weight percent platinum, and 17 g of 1-allyl-2,2,4-trimethyl-1-aza-2-silacyclopentane as prepared by Synthesis 1, at 80° C., in a 500 ml round-bottom flask fitted with a magnetic stirrer, condenser, and addition funnel, 153.44 g (1.01 mol) of 1-allyl-2,2,4-trimethyl-1-aza-2-silacyclopentane was slowly added over a 35 minute period. The resulting reaction mixture was allowed to stir at 80° C. overnight and the product was isolated by distillation at reduced pressure. The portion boiling between 78° C. and 82° C. at 0.1 mm Hg weighed 181 g and was identified as 1-(3-(2,2,4-trimethyl-1-aza-2-silacyclopentyl)propyl-1,1,3,3-tetramethyldi-siloxane.

A mixture of the 20.67 g (68.1 mmol) of 1-(3-(2,2,4-trimethyl-1-aza-2-silacyclopentyl)propyl-1,1,3,3-tetramethyldisiloxane, 10.6 g (71.5 mmol) of vinyltrimethoxysilane which had been distilled from sodium, and 0.03 g of a chloroplatinic acid-1,3-divinyl-1,1,3,3-tetramethyldisiloxane complex having about 0.7 weight percent platinum was heated for one hour at 120° C. The resulting product was distilled and the distillate was collected at 152° C. and 0.1 mm Hg. The amount of distillate collected was 28.2 g of 1-(3-(2,2,4-trimethyl-1-aza-2-silacyclopentyl)propyl)-3-(2-trimethoxysilylethyl)-1,1,3,3-tetramethyldisiloxane which was identified by $^{13}C$ and $^{29}Si$ NMR (nuclear magnetic resonance) and GC-MS.

SYNTHESIS 4

Synthesis of 1-(2-(1,2,4-trimethyl-1-aza-2silacyclopentyl)-ethyl)-3-(2-trimethoxysilylethyl)-1,1,3,3-tetramethyldisiloxane and 1-(2-(1,2,4-trimethyl-1-aza-2-silacyclopentyl)ethyl)-3-(1-trimethoxy-silylethyl)-1,1,3,3,-tetramethyldisiloxane To 59.2 g of a 2:1 mole ratio of 1-(2-trimethoxysilylethyl)-1,1,3,3-tetramethyldisiloxane and 1-(1-trimethoxysilylethyl)-1,1,3,3-tetramethyldisiloxane and 32.8 g of 1,2,4-trimethyl-2-vinyl-1-aza-2-silacyclopentane as prepared by Synthesis 2 was added 0.07 g a chloroplatinic acid-1,3-divinyl-1,1,3,3-tetramethyldisiloxane complex having about 0.7 weight percent platinum. The resulting mixture was then heated for 2 hours at 160° C. and then distilled collecting the distillate coming off at 115° C. to 125° C. and 0.1 mm Hg. The amount of distillate collected was 86.0 g and was identified by $^{13}C$ and $^{29}Si$ NMR and GC-MS to be a mixture of 1-(2-(1,2,4-trimethyl-1-aza-2-sila-cyclopentyl)ethyl)-3-(2-trimethoxysilylethyl)-1,1,3,3-tetra-methyldisiloxane and 1-(2-(1,2,4-trimethyl-1-aza-2-silacyclo-pentyl)ethyl)-3-(1-trimethoxy-silylethyl)-1,1,3,3-tetramethyldi-siloxane.

EXAMPLE 1

A base was prepared by mixing in a dental mixer, 100 parts of silanol terminated polydimethylsiloxane having a viscosity of 0.05 $m^2/s$ (square meters per second) and 1.35 parts of 1-(3-(2,2,4-trimethyl-1-aza-2-silacyclopentyl)propyl)-3-(2-trimethoxysilyl-ethyl)-1,1,3,3-tetramethyldisiloxane. This mixture was blended for 3 minutes and then 7 parts of methyltrimethoxysilane was added and mixed under vacuum. Then, 7.5 parts of fumed silica filler was added and mixed until a clear base was obtained. The resulting base was transferred to a storage tube, known as a SEMCO tube, and centrifuged to deair the base. To the desired base, 2 parts of bis-(ethoxyacetoacetonyl)-diisopropoxy titanium (IV) was added and mixed for 3 minutes. The resulting sealant was centrifuged. Test specimens were laid at 22° C. and 50% relative humidity. The properties were measured and were as shown in Table I. The surface of a test specimen was observed and the skin over time (SOT) was measured by observing the time from exposure to moisture until a finger lightly touched on the surface of the curing sealant was withdrawn without transfer of the sealant to the finger. The tack free time (TFT) was the time measured from the exposure of the sealant to moisture until a dry surface, free from tack was obtained. The durometer on the Shore A scale was measured according to ASTM Standard D-2240, the tensile strength at break in kiloPascals (kPa) and the elongation at break were measured according to ASTM Standard D-412.

EXAMPLE 2

A sealant was prepared as described in Example 1, except that 2.94 parts of 1-(3-(2,2,4-trimethyl-1-aza-2-silacyclo pentyl)propyl)-3-(2-trimethoxysilylethyl)-1,1,3,3-tetramethyldisiloxane was used instead of the 1.35 parts of Example 1. The results were as shown in Table I. The properties were measured as described in Example 1.

EXAMPLE 3

A sealant was prepared as described in Example 1, except that 2.95 parts of 1-(3-(2,2,4-trimethyl-1-aza-2-silacyclo pentyl)propyl)-3-(2-trimethoxysilylethyl)-1,1,3,3-tetramethyldisiloxane was used instead of the 1.35 parts of Example 1 and 0.67 part of bis-(ethoxyacetoacetonyl)diisopropoxy titanium (IV) was used instead of the 2 parts of Example 1. Test specimens were laid at 22° C. and 50% relative humidity and the properties were measured (Example 3). The sealant remaining in the tube was stored at 50° C. for 8 days prior to laying test samples. After the heat aging test specimens were laid at 22° C. and 50% relative humidity (Example 3A). The properties were measured as described in Example 1 and were as shown in Table I.

EXAMPLE 4

A base was prepared by mixing in a dental mixer, 100 parts of silanol terminated polydimethylsiloxane having a viscosity of 0.05 $m^2/s$ and 1.83 parts of 1-(3-(2,2,4- trimethyl-1-aza-2-silacyclopentyl)propyl)-3-(2-trimethoxysilylethyl)-1,1,3,3-tetramethyldisiloxane. This mixture was blended for 3 minutes and then 4 parts of methyltrimethoxysilane was added and mixed under vacuum. Then, 7.5 parts of fumed silica filler was added and mixed until a clear base was obtained. The resulting base was transferred to a storage tube, known as a SEMCO tube, and centrifuged to deair the base. To the deaired base, 0.25 part of bis-(ethoxyacetoacetonyl)-diisopropoxy titanium (IV) was added and mixed for 3 minutes. The resulting sealant was centrifuged. Test speciments were laid at 22° C. and 50% relative humidity. The properties were measured as described in Example 1 and were as shown in Table II.

EXAMPLE 5

A base was prepared by mixing in a dental mixer, 100 parts of silanol terminated polydimethylsiloxane having a viscosity of 0.05 m$^2$/s, 2.36 parts of 1-(3-(2,2,4-trimethyl-1-aza-2-silacyclopentyl)propyl)-3-(2-trimethoxysilylethyl)-1,1,3,3-tetramethyldisiloxane, and 0.19 part of 1,2,2,4-tetramethyl-1-aza-2-silacyclopentane. This mixture was blended for 3 minutes and then 7 parts of methyltrimethoxysilane was added and mixed under vacuum. Then, 7.5 parts of fumed silica filler was added and mixed until a clear base was obtained. The resulting base was transferred to a storage tube, known as a SEMCO tube, and centrifuged to deair the base. To the deaired base, 0.96 part of bis-(ethoxyacetoacetonyl)-diisopropoxy titanium (IV) was added and mixed for 3 minutes. The resulting sealant was centrifuged. Test specimens were laid at 22° C. and 50% relative humidity. The properties were measured as described in Example 1 and were as shown in Table II.

EXAMPLE 7

A sealant was prepared as described in Example 6, except that 0.5 part of bis-(ethoxyacetoacetonyl)-diisopropoxy titanium (IV) was used instead of the 1.9 parts of Example 6. Test specimens were laid at 22° C. and 50% relative humidity and the properties were measured as described in Example 1. The results were as shown in Table III.

EXAMPLE 8

A base was prepared by mixing in a dental mixer, 100 parts of silanol terminated polydimethylsiloxane having a viscosity of 0.05 m$^2$/s and 1.4 parts of a mixture in which the amounts were such that there were 2 moles of 1-(2-(1,2,4-trimethyl-1-aza-2-silacyclopentyl)ethyl)-3-(2-trimethoxysilylethyl)-1,1,3,3-tetramethyldisiloxane and 1 mole of 1-(2-(1,2,4-trimethyl-1-aza-2-silacyclopentyl)ethyl)-3-(1-trimethoxysilylethyl)-1,1,3,3-tetramethyldisiloxane. This mixture was blended for 3 minutes and then 4 parts of methyltrimethoxysilane was added and mixed under vacuum. Then, 8.4 parts of fumed silica filler was added and mixed until a clear base was obtained. The resulting base was transferred to a storage tube, known as a SEMCO tube, and centrifuged to deair the base. To the deaired base, 1.5 parts of bis-(ethoxyacetoacetonyl)diisopropoxy titanium (IV) was added and mixed for 3 minutes. The resulting sealant was centrifuged. Test specimens were laid at 22° C. and 50% relative humidity (Example 8). The properties were measured as described in Example 1 and were as shown in Table III. The sealant remaining in the tube was stored at 50° C. for 14 days prior to laying test samples. After the heat aging, test specimens were laid

TABLE II

| EXAMPLE | SOT minutes | TFT minutes | Durometer Shore A | Tensile Strength kPa | Elongation percent | Modulus 100% kPa |
| --- | --- | --- | --- | --- | --- | --- |
| 1 | 1 | 7 | 26 | 931 | 196 | 524 |
| 2 | 3 | 6 | 32 | 1551 | 283 | 614 |
| 3 | 7 | 16 | 23 | 662 | 124 | 607 |
| 3A | 11 | 26 | 26 | 1110 | 223 | 593 |
| 4 | 16 | 20 | 27 | 1186 | 259 | 448 |
| 5 | 10 | 15 | 18 | 793 | 239 | 352 |

EXAMPLE 6

A base was prepared by mixing in a dental mixer, 100 parts of silanol terminated polydimethylsiloxane having a viscosity of 0.05 m$^2$/s and 2.00 parts of a mixture in which the amounts were such that there were 2 moles of 1-(2-(1,2,4-trimethyl-1-aza-2-silacyclopentyl)ethyl)-3-(2-trimethoxysilylethyl)-1,1,3,3-tetramethyldisiloxane and 1 mole of 1-(2-(1,2,4-trimethyl-1-aza-2-silacyclopentyl)ethyl)-3-(1-trimethoxysilylethyl)-1,1,3,3-tetramethyldisiloxane. This mixture was blended for 3 minutes and then 4 parts of methyltrimethoxysilane was added and mixed under vacuum. Then, 7.5 parts of fumed silica filler was added and mixed until a clear base was obtained. The resulting base was transferred to a storage tube, known as a SEMCO tube, and centrifuged to deair the base. To the deaired base, 1.9 parts of bis-(ethoxyacetoacetonyl)diisopropoxy titanium (IV) was added and mixed for 3 minutes. The resulting sealant was centrifuged. Test specimens were laid at 22° C. and 50% relative humidity. The properties were measured as described in Example 1 and were as shown in Table III.

at 22° C. and 50% relative humidity (Example 8A). The results were as shown in Table III. The properties were measured as described in Example 1.

EXAMPLE 9

A base was prepared by mixing in a dental mixer, 100 parts of silanol terminated polydimethylsiloxane having a viscosity of 0.05 m$^2$/s and 2.85 parts of a mixture in which the amounts were such that there were 2 moles of 1-(2-(1,2,4-trimethyl-1-aza-2-silacyclopentyl)ethyl)-3-(2-trimethoxysilylethyl)-1,1,3,3-tetramethyldisiloxane and 1 mole of 1-(2-(1,2,4-trimethyl-1-aza-2-silacyclopentyl)ethyl)-3-(1-trimethoxysilylethyl)-1,1,3,3-tetramethyldisiloxane. This mixture was blended for 3 minutes and then 4 parts of methyltrimethoxysilane was added and mixed under vacuum. Then, 9 parts of fumed silica filler was added and mixed until a clear base was obtained. The resulting base was transferred to a storage tube, known as a SEMCO tube, and centrifuged to deair the base. To the deaired base, 2 parts of bis-(ethoxyacetoacetonyl)-diisopropoxy titanium (IV) was added and mixed for 3 minutes. The resulting sealant was centrifuged. Test specimens were laid at 22° C. and 50% relative humidity. The properties were measured as described in Example 1 and were as shown in Table III.

EXAMPLE 10

A base was prepared by mixing in a dental mixer, 100 parts of silanol terminated polydimethylsiloxane having a viscosity of 0.05 m²/s and 2.00 parts of a mixture in which the amounts were such that there were 2 moles of 1-(2-(1,2,4-trimethyl-1-aza-2-silacyclopentyl)ethyl)-3-(2-trimethoxysilylethyl)-1,1,3,3-tetramethyldisiloxane and 1 mole of 1-(2-(1,2,4-trimethyl-1-aza-2-silacyclopentyl)ethyl)-3-(1-trimethoxysilylethyl)-1,1,3,3-tetramethyldisiloxane. This mixture was blended for 3 minutes and then 7 parts of methyltrimethoxysilane was added and mixed under vacuum. Then, 9 parts of fumed silica filler was added and mixed until a clear base was obtained. The resulting base was transferred to a storage tube, known as a SEMCO tube, and centrifuged to deair the base. To the deaired base, 1.5 parts of bis-(ethoxyacetoacetonyl)-diisopropoxy titanium (IV) was added and mixed for 3 minutes. The resulting sealant was centrifuged. Test specimens were laid at 22° C. and 50% relative humidity. The properties were measured as described in Example 1 and were as shown in Table III.

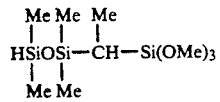

for use as the endcapper.

A polydimethylsiloxane endblocked with dimethylvinylsiloxy groups and having a viscosity of 0.05 m²/s was reacted with the above endcapper in the presence of platinum catalyst as described above. A polymer was obtained as described by the following general average formula

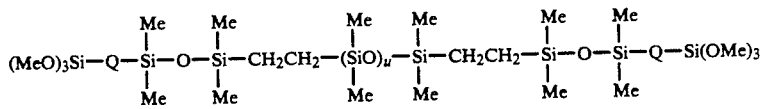

in which Q had a molar ratio of 2 moles of —CH₂CH₂— and one mole of —CH(Me)— and u had a value of about 840.

To 100 parts by weight of the above polymer were mixed in a dental mixer with 9 parts of fume silica. This base was placed under a vacuum to remove the entrapped air, and was then placed in a sealant cartridges, known as SEMCO tubes. While in the cartridges, there was added 7 parts MeSi(OMe)₃ and 2 parts of bis-(ethoxyacetoacetonyl)-diisopropoxy titanium (IV). After mixing for 3 minutes and then centrifuging, test specimens of the sealant composition were laid at 23° C.

TABLE III

| EXAMPLE | SOT minutes | TFT minutes | Durometer Shore A | Tensile Strength kPa | Elongation percent | Modulus 100% kPa |
|---|---|---|---|---|---|---|
| 6 | 7 | 18 | 30 | 972 | 177 | 627 |
| 7 | >150 | NA | 22 | 524 | 117 | 476 |
| 8 | 5 | 6 | 26 | 758 | 146 | 572 |
| 8A | — | — | 12 | 883 | 294 | 283 |
| 9 | 3 | 4 | 32 | 779 | 134 | 627 |
| 10 | 12 | 41 | 31 | 2461 | 331 | 669 |

COMPARISON EXAMPLE 1

To a 3-necked flask fitted with an air stirrer, condenser, thermometer, and positive nitrogen pressure, there were added 1340 g (10 mol) of (Me₂HSi)₂O, 740 g (5 mols) of ViSi(OMe)₃, and 40 drops of chloroplatinic acid complex of divinyltetramethyldisiloxane diluted with dimethylvinylsiloxy endblocked polydimethylsiloxane to provide 0.7 weight percent platinum. The material was then heated to 60° C. for approximately 5 hours and then stripped of excess (Me₂HSi)₂O. The yield was 1362 g of product which was a mixture having a molar ratio of two moles of the formula

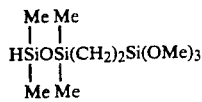

and one mole of the formula and 50% relative humidity. One of the cartridges was stored for 8 days at 50° C. (COMPARISON EXAMPLE 1A) and then the properties were measured as described in Example 1. The results observed were as shown in Table IV.

TABLE IV

| COMPARISON EX | SOT minutes | TFT minutes | Durometer Shore A | Tensile Strength kPa | Elongation percent | Modulus 100% kPa |
|---|---|---|---|---|---|---|
| 1 | 25 | 86 | 27 | 1524 | 230 | 655 |
| 1A | 21 | 57 | — | — | — | — |

That which is claimed is:

1. A polydiorganosiloxane comprising an alkoxy endblocked polydiorganosiloxane of the following general formula $$Z-(SiR_2O)_nSiR_2-Z$$

where Z is

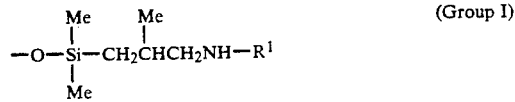

(Group I)

or

-continued $$Y - \left[ R'' - (\underset{\underset{Me}{|}}{\overset{\overset{Me}{|}}{Si}} - O)_d - \underset{\underset{Me}{|}}{\overset{\overset{Me}{|}}{Si^*}} - \right]_x X \quad \text{(Group II)}$$

where Y is $R_a(R'O)_{(3-a)}Si-$,

X is $$**-(CH_2)_p-NHCH_2CH(CH_2)_r\underset{\underset{Me}{|}}{\overset{\overset{Me}{|}}{Si}}Me_2O-,$$

$$**-(CH_2)_q\underset{\underset{CH_2CHCH_2NHR^1}{|}}{\overset{\overset{Me}{|}}{Si}}O-,$$
$$\phantom{**-(CH_2)_q Si O-}\underset{Me}{|}$$

$$**-(CH_2)_p-\overset{H}{\underset{|}{N}}-(CH_2)_r-\underset{\underset{Me}{|}}{\overset{\overset{Me}{|}}{Si}}-O-,$$

$$**-(CH_2)_q-\underset{\underset{(CH_2)_rNHR^1}{|}}{\overset{\overset{Me}{|}}{Si}}-O-\quad, \text{ or}$$

$$**-CH=CH-\underset{\underset{Me}{|}}{\overset{\overset{Me}{|}}{C}}-NH-CH_2\underset{\underset{Me}{|}}{\overset{\overset{Me}{|}}{CH}}CH_2\underset{\underset{Me}{|}}{\overset{\overset{Me}{|}}{Si}}O-$$

in which a is 0 or 1, d has a value of 1 to 3 inclusive, v is 0 or 1, n≧8, p has a value of 3 to 6 inclusive, q has a value of 2 to 6 inclusive, r has a value of 4 to 6 inclusive, w is 0 or 1, Me is methyl, $R^1$ is an alkyl radical having from 1 to 6 inclusive carbon atoms, each R is a monovalent radical independently selected from the group consisting of hydrocarbon radicals and halogenated hydrocarbon radicals, R' is an alkyl radical of 1 to 3 inclusive carbon atoms, R" is a divalent hydrocarbon radical selected from the group consisting of —(CH₂)ᵦ— and —CH(Me)(CH₂)c—, b is from 2 to 6 inclusive, c is from 0 to 4 inclusive, and the bond at ** is attached to the silicon atom Si*, in which at least one Z is of the Group II formula.

2. The polydiorganosiloxane in accordance with claim 1 in which $R^1$ is methyl.

3. The polydiorganosiloxane in accordance with claim 2 in which n has a value of from 50 to 1,000.

4. A polydiorganosiloxane mixture comprising a mixture of two types of polydiorganosiloxanes in accordance with claim 2 in which Type 1 is a polydiorganosiloxane in which both Z are Group I and Type 2 is a polydiorganosiloxane in which one Z is Group I and one Z is Group II, and further comprising a Type 3 polydiorganosiloxane in which both Z are Group I.

5. The polydiorganosiloxane in accordance with claim 2 in which R and R' are methyl radicals.

6. The polydiorganosiloxane in accordance with claim 3 in which R and R' are methyl radicals.

7. The polydiorganosiloxane in accordance with claim 4 in which R and R' are methyl radicals.

8. The polydiorganosiloxane in accordance with claim 2 in which R" is a mixture of —CH₂CH₂— and —CH(Me)—.

9. The polydiorganosiloxane in accordance with claim 6 in which R" is a mixture of —CH₂CH₂— and —CH(Me)—.

10. The polydiorganosiloxane in accordance with claim 7 in which R" is a mixture of —CH₂CH₂— and —CH(Me)—.

11. The polydiorganosiloxane in accordance with claim 2 in which X is $$**-(CH_2)_p-NHCH_2\underset{\underset{Me}{|}}{\overset{\overset{Me}{|}}{CH}}CH_2SiMe_2O-$$

a is 0, and p is 3.

12. The polydiorganosiloxane in accordance with claim 6 in which X is $$**-(CH_2)_p-NHCH_2\underset{\underset{Me}{|}}{\overset{\overset{Me}{|}}{CH}}CH_2SiMe_2O-$$

a is 0, and p is 3.

13. The polydiorganosiloxane in accordance with claim 8 in which X is $$**-(CH_2)_p-NHCH_2\underset{\underset{Me}{|}}{\overset{\overset{Me}{|}}{CH}}CH_2SiMe_2O-$$

a is 0, and p is 3.

14. The polydiorganosiloxane in accordance with claim 9 in which X is $$**-(CH_2)_p-NHCH_2\underset{\underset{Me}{|}}{\overset{\overset{Me}{|}}{CH}}CH_2SiMe_2O-$$

a is 0, and p is 3.

15. The polydiorganosiloxane in accordance with claim 2 in which X is $$**-(CH_2)_q\underset{\underset{CH_2CHCH_2NHMe}{|}}{\overset{\overset{Me}{|}}{Si}}O-$$
$$\phantom{**-(CH_2)_q Si O-}\underset{Me}{|}$$

a is 0, and q is 2.

16. The polydiorganosiloxane in accordance with claim 6 in which X is $$**-(CH_2)_q\underset{\underset{CH_2CHCH_2NHMe}{|}}{\overset{\overset{Me}{|}}{Si}}O-$$
$$\phantom{**-(CH_2)_q Si O-}\underset{Me}{|}$$

a is 0, and q is 2.

17. The polydiorganosiloxane in accordance with claim 8 in which X is 5,276,123

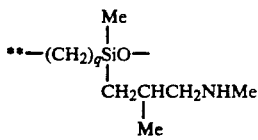

a is 0, and q is 2.

18. The polydiorganosiloxane in accordance with claim 9 in which X is

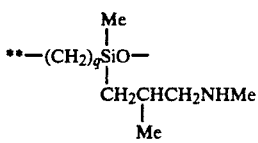

a is 0, and q is 2.

19. A method of preparing alkoxy endblocked polydiorganosiloxanes comprising mixing an azasilacycloalkyl functional alkoxysilane selected from the group consisting of

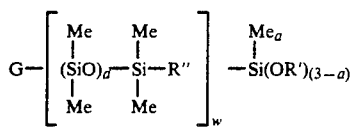

in which G is an azasilacycloalkyl group selected from the group consisting of

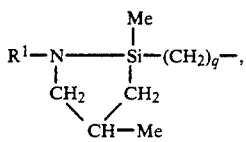

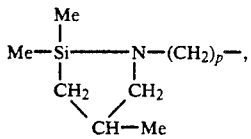

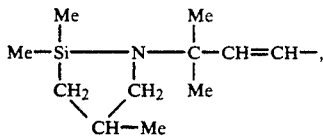

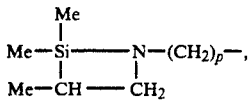

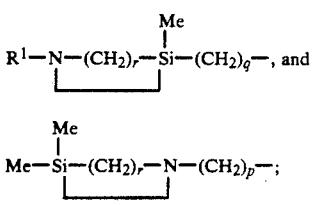

in which $R^1$ is an alkyl radical having from 1 to 6 inclusive carbon atoms, $R'$ is an alkyl radical of from 1 to 3 carbon atoms, $R''$ is a divalent hydrocarbon radical selected from the group consisting of —$(CH_2)_b$— and —$CH(Me)(CH_2)_c$—, b is from 2 to 6 inclusive, c is from 0 to 4 inclusive, Me is methyl, a is 0 or 1, d has a value of 1 to 3 inclusive, w is 0 or 1, p has a value of 3 to 6 inclusive, q has a value of 2 to 6 inclusive, and r has a value of 4 to 6 inclusive with a silanol terminated polydiorganosiloxane of the general formula $$HO-(SiR_2O)_nSiR_2OH$$

where each R is a monovalent hydrocarbon radical independently selected from the group consisting of hydrocarbon radicals and halogenated hydrocarbon radicals and $n \geq 8$, and the azasilacycloalkyl functional alkoxysilane reacts with the silanol terminated polydiorganosiloxane producing an alkoxy endblocked polydiorganosiloxane of the following general formula $$Z-(SiR_2O)_nSiR_2-Z$$

where Z is

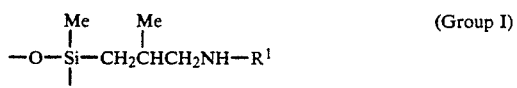 (Group I)

or

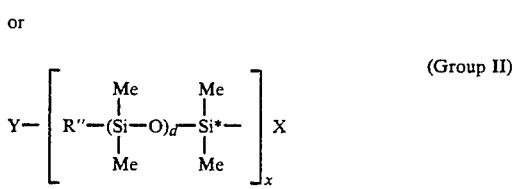 (Group II)

where Y is $$R_a(R'O)_{(3-a)}Si-,$$

X is

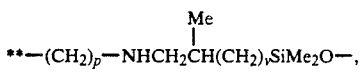

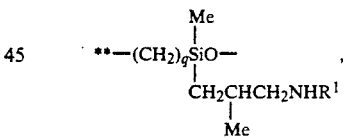

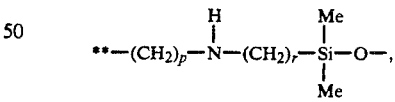

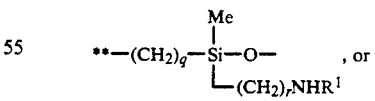

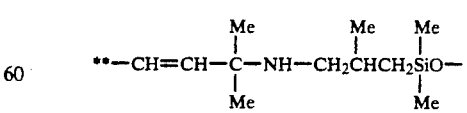

in which a is 0 or 1, d has a value of 1 to 3 inclusive, v is 0 or 1, $n \geq 8$, p has a value of 3 to 6 inclusive, q has a value of 2 to 6 inclusive, r has a value of 4 to 6 inclusive, w is 0 or 1, Me is methyl, $R^1$ is an alkyl radical having from 1 to 6 inclusive carbon atoms, each R is a monovalent radical independently selected from the group consisting of hydrocarbon radicals and halogenated hydrocarbon radicals, R' is an alkyl radical of 1 to 3 inclusive carbon atoms, R" is a divalent hydrocarbon radical 3 inclusive carbon atoms, R" is a divalent hydrocarbon radical selected from the group consisting of —(CH$_2$)$_b$— and —CH(Me)(CH$_2$)$_c$—, b is from 2 to 6 inclusive, c is from 0 to 4 inclusive, and the bond at ** is attached to the silicon atom Si*, in which at least one Z is of the Group II formula.

20. The method according to claim 19 in which R$^1$ is methyl.

21. The method according to claim 20 in which n has a value of from 50 to 1,000.

22. The method according to claim 20 further comprising mixing with the azasilacyclopentyl functional alkoxysilane and silanol terminated polydiorganosiloxane, 1,2,2,4-tetramethyl-1-aza-2-silacyclopentane.

23. The method according to claim 20 in which R and R' are methyl radicals.

24. The method according to claim 21 in which R and R' are methyl radicals.

25. The method according to claim 20 in which R" is a mixture of —CH$_2$CH$_2$— and —CH(Me)—.

26. The method according to claim 24 in which R" is a mixture of —CH$_2$CH$_2$— and —CH(Me)—.

27. The method according to claim 20 in which a is 0 and p is 3.

28. The method according to claim 24 in which a is 0 and p is 3.

29. The method according to claim 25 in which a is 0 and p is 3.

30. The method according to claim 26 in which a is 0 and p is 3.

31. The method according to claim 20 in which a is 0 and q is 2.

32. The method according to claim 24 in which a is 0 and q is 2.

33. The method according to claim 25 in which a is 0 and q is 2.

34. The method according to claim 26 in which a is 0 and q is 2.

35. A one package room temperature vulcanizable silicone elastomer comprising a product which is storage stable in the absence of moisture and curable to an elastomeric product when exposed to moisture and obtained by mixing (A) an alkoxy endblocked polydiorganosiloxane of the following general formula Z—(SiR$_2$O)$_n$SiR$_2$—Z where Z is

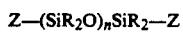

(Group I)

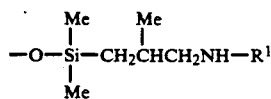

or

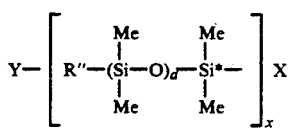

(Group II)

where Y is $R_a(R'O)_{(3-a)}Si—$,

X is

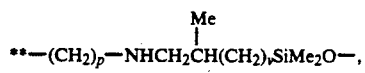

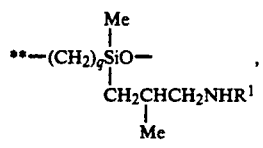

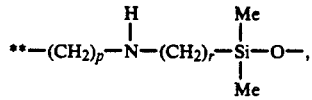

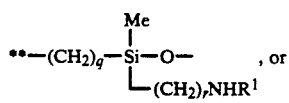, or

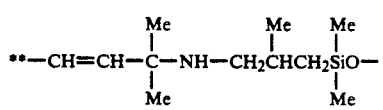

in which a is 0 or 1, d has a value of 1 to 3 inclusive, v is 0 or 1, n≥8, p has a value of 3 to 6 inclusive, q has a value of 2 to 6 inclusive, r has a value of 4 to 6 inclusive, w is 0 or 1, Me is methyl, R$^1$ is an alkyl radical having from 1 to 6 inclusive carbon atoms, each R is a monovalent radical independently selected from the group consisting of hydrocarbon radicals and halogenated hydrocarbon radicals, R' is an alkyl radical of 1 to 3 inclusive carbon atoms, R" is a divalent hydrocarbon radical selected from the group consisting of —(CH$_2$)$_b$— and —CH(Me)(CH$_2$)$_c$—, b is from 2 to 6 inclusive, c is from 0 to 4 inclusive, the bond at ** is attached to the silicon atom Si*, and in the alkoxy endblocked polydiorganosiloxane at least one Z is Group II, (B) an alkoxysilane,
(C) a titanium catalyst, and
(D) a filler.

36. The one package room temperature vulcanizable silicone elastomer in accordance with claim 35 in which R$^1$ is methyl.

37. The one package room temperature vulcanizable silicone elastomer in accordance with claim 36 in which n has a value of from 50 to 1000.

38. The one package room temperature vulcanizable silicone elastomer in accordance with claim 37 in which R and R' are methyl radicals.

39. The one package room temperature vulcanizable silicone elastomer in accordance with claim 36 in which R" is a mixture of —CH$_2$CH$_2$— and —CH(Me)—.

40. The one package room temperature vulcanizable silicone elastomer in accordance with claim 38 in which R" is a mixture of —CH$_2$CH$_2$— and —CH(Me)—.

41. The one package room temperature vulcanizable silicone elastomer in accordance with claim 36 in which X is

a is 0, and p is 3.

42. The one package room temperature vulcanizable silicone elastomer in accordance with claim 38 in which X is

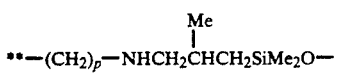

a is 0, and p is 3.

43. The one package room temperature vulcanizable silicone elastomer in accordance with claim 39 in which X is

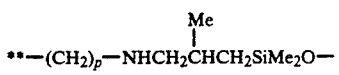

a is 0, and p is 3.

44. The one package room temperature vulcanizable silicone elastomer in accordance with claim 40 in which X is

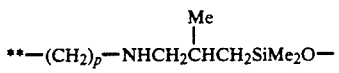

a is 0, and p is 3.

45. The one package room temperature vulcanizable silicone elastomer in accordance with claim 36 in which X is

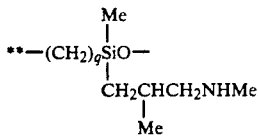

a is 0, and q is 2.

46. The one package room temperature vulcanizable silicone elastomer in accordance with claim 38 in which X is

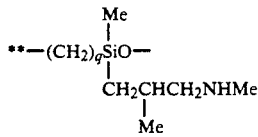

a is 0, and q is 2.

47. The one package room temperature vulcanizable silicone elastomer in accordance with claim 39 in which X is

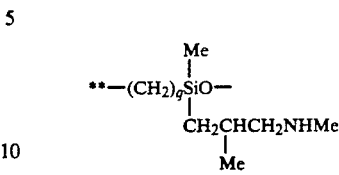

a is 0, and q is 2.

48. The one package room temperature vulcanizable silicone elastomer in accordance with claim 40 in which X is

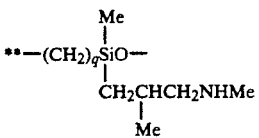

a is 0, and q is 2.

49. The one package room temperature vulcanizable silicone elastomer in accordance with claim 37 in which the alkoxysilane of (B) has a formula $R_xSi(OR')_{4-x}$ where x is 0 or 1, where R and R' have the same meaning as in claim 35.

50. The one package room temperature vulcanizable silicone elastomer in accordance with claim 49 in which R and R' are methyl radicals and x is 1.

51. The one package room temperature vulcanizable silicone elastomer in accordance with claim 50 in which the titanium catalyst of (C) is a di-carbonyl titanium compound.

52. The one package room temperature vulcanizable silicone elastomer in accordance with claim 38 in which the alkoxysilane of (B) is methyltrimethoxysilane.

53. The one package room temperature vulcanizable silicone elastomer in accordance with claim 40 in which the alkoxysilane of (B) is methyltrimethoxysilane.

54. The one package room temperature vulcanizable silicone elastomer in accordance with claim 41 in which the alkoxysilane of (B) is methyltrimethoxysilane.

55. The one package room temperature vulcanizable silicone elastomer in accordance with claim 48 in which the alkoxysilane of (B) is methyltrimethoxysilane.

* * * * *